United States Patent
von Malmborg et al.

(10) Patent No.: US 6,908,442 B2
(45) Date of Patent: Jun. 21, 2005

(54) BENDING RESISTANT MALE CONNECTOR FOR A GUIDE WIRE

(75) Inventors: Paer von Malmborg, Uppsala (SE); Ola Hammarstroem, Lerdala (SE); Paer Gustafsson, Uppsala (SE)

(73) Assignee: Radi Medical Systems AB, Uppsala (SE)

(*) Notice: Subject to any disclaimer, the term of this patent is extended or adjusted under 35 U.S.C. 154(b) by 57 days.

(21) Appl. No.: 09/986,117

(22) Filed: Nov. 7, 2001

(65) Prior Publication Data

US 2003/0088193 A1 May 8, 2003

(51) Int. Cl.⁷ .......................... A61B 5/00; A61M 25/00
(52) U.S. Cl. ............................................................ 600/585
(58) Field of Search ................................ 600/433, 434, 600/437, 459, 462, 466, 506, 585; 604/95, 96, 280, 281; 607/116, 122, 124

(56) References Cited

U.S. PATENT DOCUMENTS

| | | | | |
|---|---|---|---|---|
| 3,991,745 A | * | 11/1976 | Yoslow et al. | 600/594 |
| 5,178,159 A | | 1/1993 | Christian | 128/772 |
| 5,382,238 A | * | 1/1995 | Abrahamson et al. | 604/170.01 |
| 5,501,228 A | * | 3/1996 | Lafontaine et al. | 600/505 |
| 5,938,624 A | * | 8/1999 | Akerfeldt et al. | 600/585 |
| 6,142,958 A | * | 11/2000 | Hammarstrom et al. | 600/585 |
| 6,196,980 B1 | | 3/2001 | Akerfeldt et al. | |
| 6,210,339 B1 | | 4/2001 | Kiepen et al. | |
| 6,371,972 B1 | * | 4/2002 | Wallace et al. | 606/200 |
| 6,373,705 B1 | * | 4/2002 | Koelle et al. | 361/720 |

FOREIGN PATENT DOCUMENTS

| | | |
|---|---|---|
| EP | 0 616 794 A1 | 9/1994 |
| EP | 0 925 803 A2 | 6/1999 |

* cited by examiner

Primary Examiner—Max F. Hindenburg
Assistant Examiner—Jonathan Foreman
(74) Attorney, Agent, or Firm—Foley & Lardner LLP

(57) ABSTRACT

During use there is a risk that a male connector for a guide wire is bent. With the present male connector (1) more material with high modulus of elasticity can be provided inside the male connector (1), which makes the male connector (1) more bending resistant. The male connector (1) comprises a core wire (3), a plurality of conductive members (4) spaced apart longitudinally along said core wire (3), a plurality of conductors (5) disposed along the core wire (3), each of the conductors (5) being connected to a respective conductive member (4). The core wire (3) has such a shape that least one longitudinal cavity is provided, which longitudinal cavity remains substantially intact when the male connector (1) is bent, thereby protecting the conductors (5), which are disposed in said cavity, from being damaged.

33 Claims, 3 Drawing Sheets

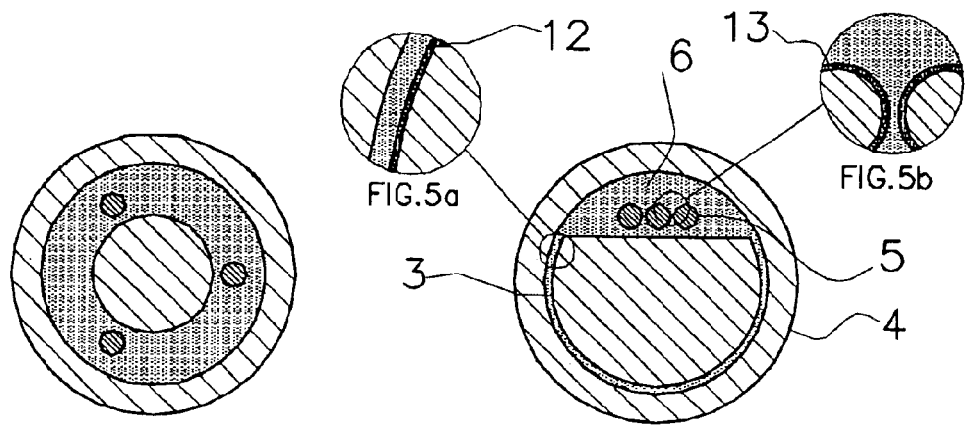
FIG. 4 (Prior art)
FIG. 5
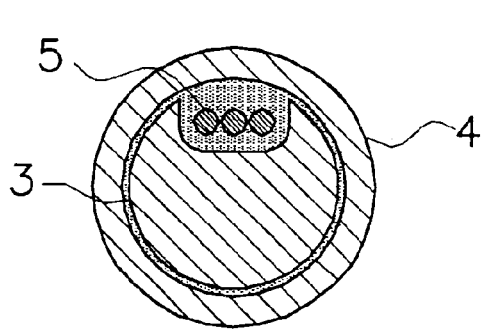
FIG. 6
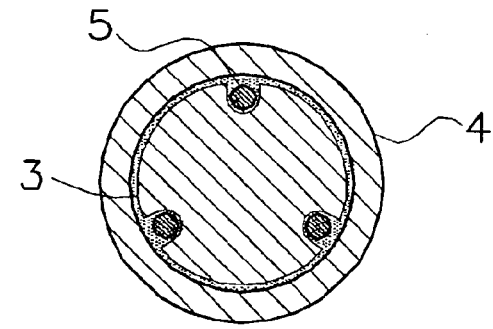
FIG. 7
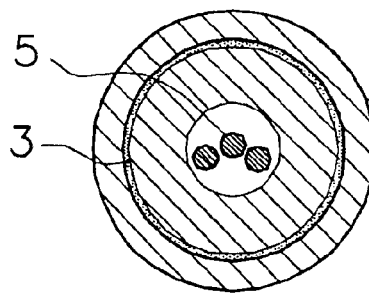
FIG. 8
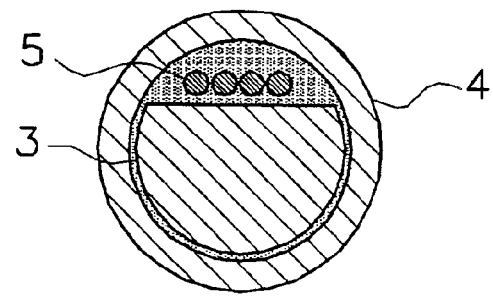
FIG. 10

US 6,908,442 B2

BENDING RESISTANT MALE CONNECTOR FOR A GUIDE WIRE

FIELD OF THE INVENTION

The present invention relates to a bending resistant male connector for a guide wire, and in particular to a bending resistant male connector having a core wire with such a shape that the total configuration consisting of the core wire, conductors and insulating material makes an optimal use of the available space inside the male connector.

BACKGROUND OF THE INVENTION

Guide wires are generally known in the art. They are, for example, used in connection with the treatment of coronary diseases, where an x-ray of a blood vessel may be done to detect the presence of an occlusion, which, however, does not show the cross section of a stenosis. It is accepted that the best way to diagnose the significance of the stenosis is to perform a measurement of the blood pressure upstream and downstream of the stenosis. In this case, a guide wire is used to position a pressure-measuring sensor in the area of interest. Once the guide wire is positioned, a catheter is slid over the guide wire and a balloon dilation may then be done. The electrical signals from the pressure-measuring sensor at the distal end of the guide wire are lead through conductors embedded in the guide wire to a male connector at the proximal end of the guide wire. In use, the male connector is connected to a female connector and the signals from the pressure-measuring sensor are transferred to an interface, which converts the signals and presents them in the desired form for an operator.

The male connector disposed at the proximal end of the guide wire comprises basically a core wire, a plurality of conductors, a plurality of conductive members, and insulating material therebetween. When the male connector is connected to the female connector, the conductive members transfer the electrical signals from the conductors of the male connector to similar conductive members inside the female connector. The core wire, which conventionally extends through the guide wire, is used to prevent kinks, to provide strength to the guide wire and to hold the guide wire together. Especially when the male connector is inserted into the female connector, there exists a substantial risk of over-bending the male connector or damaging the thin conductors inside the male connector. The core wire inside the male connector is therefore normally made of a material with high modulus of elasticity, such as stainless steel. Examples of such male connectors are disclosed in U.S. Pat. Nos. 5,178,159 and 5,938,624.

From the above, it should be obvious that the core wire should be as large as possible, so that a large amount of high strength material is provided inside the male connector, while leaving enough room for the conductors and insulation to fit within the guide wire. In U.S. Pat. Nos. 5,178,159 and 5,938,624 it is assumed that the core wire is cylindrical and that the conductors are disposed at the outside of the core wire. With this shape of the core wire, the total configuration consisting of the core wire and the conductors will occupy a large part of the space inside the male connector, without the core wire and the thin conductors themselves actually utilizing an optimum of the available space, or, with other words, there is an excess of insulating material inside the male connector. Here it should be mentioned that the available space inside the guide wire is limited by the diameter of the catheter that is slid over the guide wire. Since the catheter also is slid over the male connector, which extends from the proximal end of the guide wire, the size of the entire male connector is also limited by the diameter of this catheter. The nominal diameter of a conventional small catheter may be as small as 0.355 mm, which provides an upper limit for the diameter of a male connector used together with such a catheter.

As mentioned above, the core wire conventionally extends through the guide wire, all the way from the sensor at the distal end of the guide wire to the male connector at the proximal end of the guide wire, where the core wire provides stiffness to the male connector. For such a long core wire, the most economical and practical shape of the core wire is cylindrical, and the conventional thinking has been to keep the cylindrical shape of the core wire also inside the male connector, despite the disadvantage that the total configuration consisting of the core wire and the conductors occupies less than the optimum of the available space, which involves the risk that the male connector will be bent or damaged when inserted into the female connector.

Consequently, there exists a need for a male connector having a core wire with such a shape that the total configuration consisting of the core wire, conductors and insulating material makes an optimal use of the available space inside the male connector. In order to keep the cylindrical shape of the part of the core wire that extends from the male connector to the sensor, the male connector should preferably constitute a separate unit, which can be mounted at the proximal end of an existing guide wire. Obviously, the last requirement implies that the core wire inside the male connector is different from the core wire inside the rest of the guide wire.

SUMMARY OF THE INVENTION

The main object of the present invention is to provide a male connector having a core wire with such a shape that more material with high modulus of elasticity can be provided inside the male connector, while still leaving enough space for the conductors.

A second object of the present invention is to provide a male connector which is durable and resistant against bending, and which is easy to insert into a female connector without bending.

A third object of the present invention is to provide a male connector having a core wire with such a shape that the conductors are protected from damage even if the male connector is bent.

A fourth object of the present invention is to provide a male connector that allows a long insulation distance between the conductive members with preserved stiffness.

A fifth object of the present invention is to provide a male connector that is separately mountable on an existing guide wire.

A sixth object of the present invention is to provide a male connector that allows filling of insulation material with a minimum of voids, which yields a waterproof and constant quality design.

These objects are achieved with a male connector as defined in claim 1. Preferred embodiments of the male connector according to the invention are defined in the dependent claims.

A preferred embodiment of the male connector according to the present invention comprises a core wire, a plurality of conductive members, a plurality of conductors, and insulating material. Each of the conductors is connected to a respective conductive member. The conductive members, which are annular with the same outer diameter as the guide wire, are spaced apart longitudinally from each other. The core wire is not cylindrical, but a part of its mantel surface is flat, thereby giving the core wire a D-shaped cross section.

When the male connector is assembled, the conductors are positioned outside the straight leg of the D-shaped cross section. When the male connector has been attached to the proximal end of a guide wire and the D-shaped core wire has been inserted a small distance into the guide wire, the conductors at the distal end of the male connector are therefore positioned in the elongated cavity created between the inner surface of the cylindrical guide wire and the D-shaped core wire. The more proximal sections of the conductors that are inside the annular conductive members are in the corresponding way positioned in the cavities created between the conductive members and the D-shaped core wire.

BRIEF DESCRIPTION OF THE DRAWINGS

FIG. 4 shows the cross section of a male connector according to prior art.

FIG. 5 shows the cross section of a first embodiment of a male connector according to the present invention.

FIG. 5a shows an enlarged part of the core wire of FIG. 5.

FIG. 5b shows an enlarged part of the conductors of FIG. 5.

FIG. 6 shows the cross section of a second embodiment of a male connector according to the present invention.

FIG. 7 shows the cross section of a third embodiment of a male connector according to the present invention.

FIG. 8 shows the cross section of a fourth embodiment of a male connector according to the present invention.

FIG. 10 shows the cross section of the male connector according to FIG. 9.

DETAILED DESCRIPTION OF THE DRAWINGS

Figure 1:
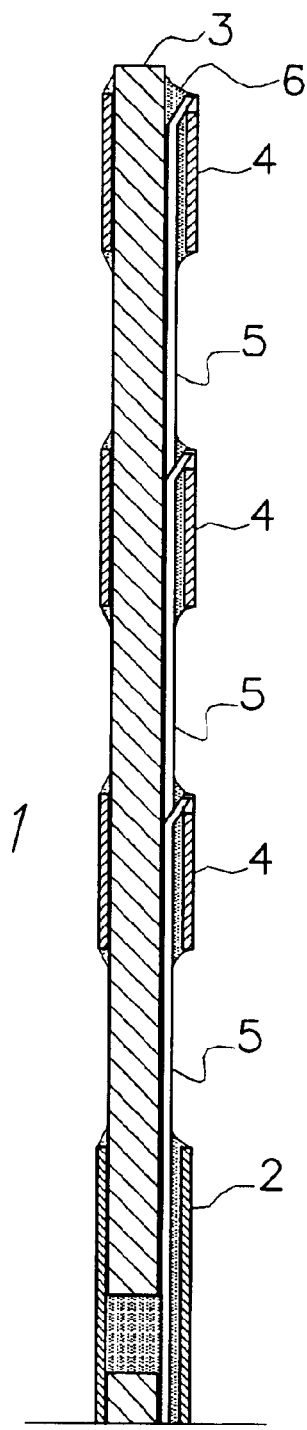
FIG. 1 illustrates a male connector according to the present invention mounted on a guide wire.

FIG. 1 illustrates a male connector 1 according to the present invention. The male connector 1 is disposed on the proximal end of a guide wire 2. The male connector 1 comprises basically a core wire 3, a plurality of conductive members 4, and plurality of conductors 5.

The conductive members 4, which are annular with the same outer diameter as the guide wire 2, are spaced apart longitudinally from each other. When the male connector 1 is assembled, each of the conductors 5 is electrically connected to a respective conductive member 4 and insulating material 6 is provided between the core wire 3 and the conductive members 4. The insulating material 6 fixates the conductors 5 inside the conductive members 4 and insulates the conductive members 4 from the core wire 3.

Figure 2:
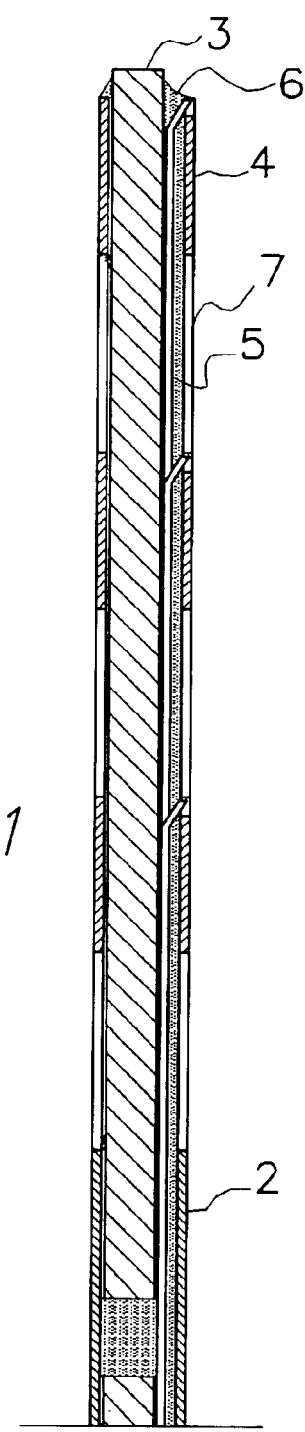
FIG. 2 illustrates the male connector of FIG. 1 provided with extra insulating material.

In FIG. 2, the male connector 1 of FIG. 1 has been provided with an extra continuous outer insulating material 7, the outer surface of which being coextensive with the outer surfaces of the conductive members 4. The insulating material 7 insulates the conductors 5 and the conductive members 4 from each other, and provides the male connector with additional stiffness.

Note that in FIGS. 1 and 2 there is a small gap provided between the core wire 3 of the male connector 1 and the core wire that extends through the rest of the guide wire 2, i.e. the core wire 3 of the male connector 1 is not an integral part of the core wire in the more distal and much longer part of the guide wire 2 that is not shown in FIG. 1 or FIG. 2. Consequently, this small gap indicates that the male connector 1 can be regarded as a separate part of the overall guide wire assembly, which is in contrast to the prior art designs. The special advantages with this feature will be described below.

From FIG. 1 and FIG. 2 it should be noted that the proximal end of a conductor 5 is connected the proximal end of the corresponding conductive member 4, i.e. the adjacent proximal part of the conductor 5 is supported by the conductive member 4 and the insulating material 6 inside this conductive member 4. The conductive members 4 are relatively stiff, and, when the male connector 1 is bent, the connections between the conductive members 4 and the conductors 5 are therefore experiencing less bending stress than they would do if the conductors 5 were attached to the distal ends of the conductive members 4.

Figure 3:
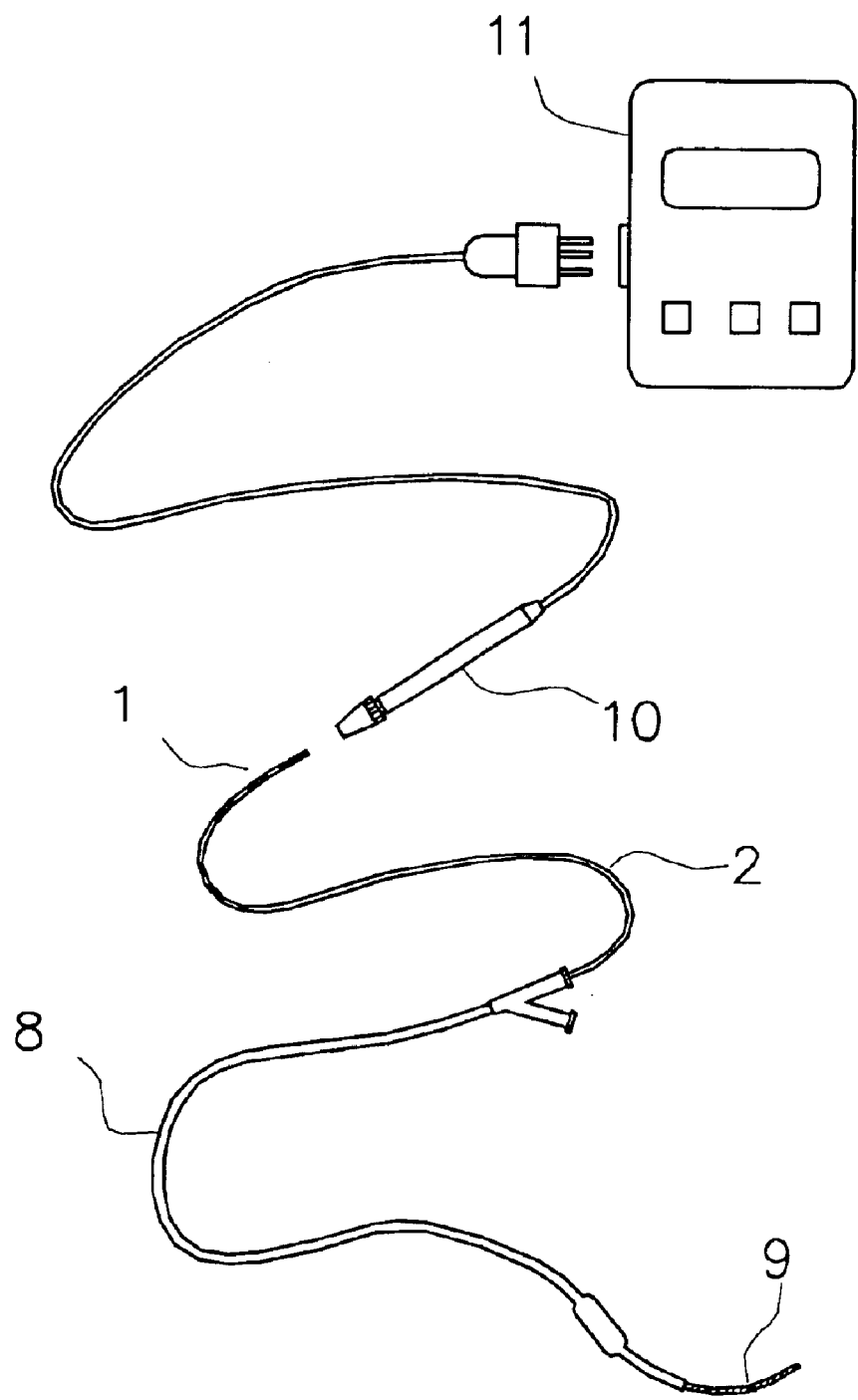
FIG. 3 illustrates a guide wire with a male connector used within a catheter, and a female connector connected to a monitor.

The overall guide wire assembly is illustrated in FIG. 3, where a male connector 1 is attached to the proximal end of a guide wire 2. The guide wire 2 is inserted within a balloon catheter 8. At the distal end of the guide wire 2 is a sensor 9. The male connector 1 is inserted into a female connector 10. The female connector 10 is electrically connectable into a monitor device 11. In practice, the distal end of the guide wire 2 is inserted into the body, for example into an opening into the femoral artery. Once positioned by a physician at the appropriate location, a catheter 8 of the desired type is guided onto the guide wire 2. In use, the signals from the sensor 9 are lead by the conductors enclosed in the guide wire 2 to the conductive members of the male connector 1. The signals are then transferred from the conductive members of the male connector 1 to similar conductive members inside the female connector 10. The signals are then presented for the physician by the monitor device 11.

FIG. 4 shows the cross section of a male connector according to a prior art design. In this case, three conductors are symmetrically disposed around a cylindrical core wire positioned eccentrically in the male connector. A conductive member surrounds the core wire and the three conductors, and insulating material fills the rest of the space inside the male connector. A major disadvantage with such a prior art design is that if the male connector illustrated in FIG. 4 is bent, for instance during insertion into a female connector, all parts of the male connector will experience a bending stress. In this case, the thin and sensitive conductors embedded in the relatively soft insulating material may be squeezed between the harder core wire and conductive member, which involves the risk that one or several of these conductors will be damaged or break.

In FIG. 5 the cross section of a preferred embodiment of a male connector according to the present invention is illustrated. In this case, a core wire 3 having a homogeneous D-shaped cross section constitutes the central part of a male connector. In this case, three conductors 5 are positioned outside the flat part of the D-shaped core wire 3, and a cylindrical conductive member 4 surrounds the conductors 5 and the D-shaped core wire 3. The rest of the space inside the cylindrical conductive member 4 is filled with insulating material 6, with a minimum of insulating material 6 being provided between the conductive member 4 and the curved part of the D-shaped core wire 3.

It should be noted that the D-shape of the core wire 3 provides a cavity between the inner surface of the cylindrical conductive member 4 and the flat part of the D-shaped core wire 3. This cavity, in which the conductors 5 are disposed, will remain practically intact even when the male connector is bent. This means that even if a bending stress is imposed on the male connector, there is no risk that the conductors 5 will be squeezed between the core wire 3 and the conductive member 4, which obviously prevents the conductors 5 from being damaged during, for example, insertion into a female connector. From FIG. 5 it should be obvious that a requirement for such a protecting cavity is that the ends of the straight leg of the D-shaped cross section are positioned near the conductive member 4, i.e. there is a minimum of insulating material 6 between the inner surface of the conductive member 4 and these parts of the D-shaped core wire 3. Note that herein, the term "cavity" should not be taken literally. As is apparent from FIG. 5, also the cavity is filled with the continuous insulating material 6.

An enlarged part of the core wire 3 of FIG. 5 is illustrated in FIG. 5*a*. FIG. 5*a* shows that the core wire 3 is provided with a separate layer of insulating material 12. The core wire 3 may therefore be regarded as an insulated core wire 3, and the amount of insulating material 6 being provided between the curved part of the D-shaped core wire 3 and the conductive member 4 can practically be reduced to zero. An example of such an insulating material 12 is ceramic particles contained in a polymer matrix. As an alternative, the insulating material 12 can consist of a metal oxidized to ceramic state. For instance, the core wire 3 could be made of titanium, the surface of which is oxidized to titanium dioxide, or the core wire 3 could be made of a metal having a coating of aluminium oxidized to $Al_2O_3$. It is also possible to manufacture the core wire 3 from an insulating material, in which case no insulating material has to be provided between the curved part of the D-shaped core wire 3 and the conductive members 4. With the proper choice of material for the core wire 3 and/or the insulating material 12, the conductors 5 may be connected to the conductive members 4 by a crimping technique.

In FIG. 5*b* an enlarged part of the conductors 5 of FIG. 5 is illustrated. FIG. 5*b* shows that the conductors 5 each are provided with a separate layer of insulating material 13. The conductors 5 may therefore be regarded as insulated conductors 5, which means that conductors 5 may be positioned very close to each other, i.e. without insulating material 6 being provided between them.

As mentioned above, the conventional design of a male connector for a guide wire is to let the core wire extend into the male connector, i.e. the core wire of the male connector is an integral part of the core wire in the guide wire. As an example, since the guide wire may be rather long and thin, up to 300 cm long and 0.355 mm in diameter, it seems practical and economical to have a cylindrical core wire inside the guide wire. The core wire in such a conventional 0.355 mm guide wire has typically a diameter of only 0.15 mm. To let such a thin cylindrical core wire extend into a male connector and simply flatten a part of the mantle surface of the core wire in order to create a D-shaped cross section would not provide the special advantages described above. This fact is easy to recognize from FIG. 4, where a core wire according to a conventional design is illustrated. To just strip off a part of the mantle surface of a core wire having such a small diameter would obviously not create a cavity in which the conductors could reside without the risk of being damaged when the male connector is bent. Although it is conceivable, and within the scope of the present invention, to enlarge the part of the core wire that extends into the male connector and form this part into the desired cross section, such as a D-shaped cross section, a better solution is to provide male connector which is separately mountable on an existing guide wire.

In FIG. 6 the cross section of a first alternative embodiment of the male connector according to the present invention is illustrated. In this embodiment, the core wire 3 has been provided with a trough-shaped recess, in which the conductors 5 are accommodated. The cavity created by this trough-shaped recess would obviously protect the conductors 5 from being squeezed between the conductive member 4 and the core wire 3 if the male connector is bent.

In FIG. 6, the conductors 5 are all positioned in a common cavity created by a single recess in the mantle surface of the core wire 3. However, each of the connectors 5 could be positioned in a separate cavity. This type of configuration is illustrated in FIG. 7, where three recesses are provided in the mantle surface of the core wire 3. Each of these three recesses accommodates a single conductor 5.

As mentioned above, the main object of the present invention is to provide a male connector having a core wire with such a shape that a large amount of material with high modulus of elasticity can be provided inside the male connector, so that core wire, and therefore the male connector, is as stiff as possible. In accordance with this object, it is also conceivable to replace the recesses described above with one or several longitudinal holes, in which the conductors are disposed. An example of such a configuration is shown in FIG. 8, where the core wire 3 has been provided with a cavity in the form of a central hole, in which the conductors 5 are accommodated.

From the illustrated embodiments of the present invention it should be obvious that from a manufacturing point of view the conductive members 4 may be regarded as resting against the core wire 3, since at least two points on the mantle surface of the core wire 3 have such positions that there is only one way to radially position the core wire 3 inside the conductive member 4. The core wire 3 may therefore be described as a self-centering or self-positioning core wire 3, and, consequently, no extra positioning step is necessary in the manufacturing of the present male connector 1. From FIG. 4 it should be obvious that this advantage is in contrast to prior art designs, in which the core wire has to be carefully positioned in the centre of the conductive member, or at some other location inside the conductive member.

Figure 9:
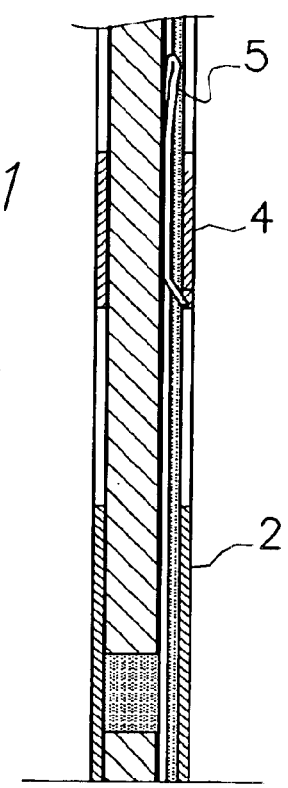
FIG. 9 illustrates a male connector having an alternative conductor configuration.

In FIG. 9 a male connector 1 with another configuration of the conductors 5 is illustrated. In the depicted configuration, each of the conductors 5 is drawn in a 180° loop before being connected to the respective conductive member 4. Tests have shown that this loop, which extends in the proximal direction of the male connector 1 before going back to the distal end of the conductive member 4, where the conductor 5 is connected, further improves the durability of the conductors 5. Especially when the conductor arrangement according to FIG. 9 is combined with one of the core wire cross sections described above a surprisingly bending insensitive male connector is provided.

A cross section of the conductor arrangement of FIG. 9 will obviously exhibit an extra conductor cross section, since each conductor loop contains two conductors, one going in the forward direction and one going in the backward direction. An example of such a cross section is shown in FIG. 10, where the D-shaped core wire according to FIG. 5 has been combined with the conductor arrangement according to FIG. 9. In this case, the three conductors 5 give rise to four conductor cross-sections inside the conductive member 4.

To summarize, with the present male connector, which has such a design that the total configuration consisting of the core wire and the conductors presents a substantially circular cross section, more material with high modulus of elasticity can be provided in the interior of the male connector, in comparison with prior art designs. This feature makes the male connector according to the invention durable and resistant against bending, which, in turn, makes it easy to insert the male connector into a female connector, with a minimum risk of bending the male connector and thereby damaging the conductors or other parts of the male connector.

Further, with a larger amount of material with high modulus of elasticity, the male connector becomes stiffer, which allows a long insulation distance between the longitudinally spaced apart annular conductive members with preserved stiffness. This is an advantage since a long insulation distance means that the risk of leakage currents between the conductive members is minimized.

Still further, with a larger amount of material with high modulus of elasticity, the amount of insulating material inside the male connector becomes less, which allows filling of insulation material with a minimum of voids, which, in turn, yields a waterproof and constant quality design.

Although the present invention has been described with reference to specific embodiments, also shown in the appended drawings, it will be apparent for those skilled in the art that many variations and modifications can be done within the scope of the invention as described in the specification and defined in the following claims.

What is claimed is:

1. Male connector (1) for a guide wire (2), wherein
   the guide wire (2) comprises a guide wire core including a section that substantially extends through the guide wire (2) between a sensor at a distal end of the guide wire (2) and the male connector (1) at a proximal end of the guide wire (2), wherein
   the male connector (1) comprises a core wire (3), a plurality of conductive members (4) spaced apart longitudinally along said core wire (3), and a plurality of conductors (5) disposed along the core wire (3), each of the conductors (5) being connected to a respective conductive member (4), wherein the core wire (3) has such a shape that at least one longitudinal cavity is provided inside the male connector (1), the longitudinal cavity being adapted to remain substantially intact when the male connector (1) is bent, thereby protecting the conductors (5), which are disposed in said cavity, from being damaged if the male connector (1) is bent, wherein the core wire does not have a solid circular cross section, and wherein the core wire (3) is stiffer than the section of the guide wire core that substantially extends through the guide wire (2) substantially from the distal end of the guide wire (2) substantially to the proximal end of the guide wire (2).

2. The male connector (1) according to claim 1, wherein the core wire (3) has a D-shaped cross section, and wherein said cavity is provided between an inner surface of the cylindrical conductive members (4) and the flat part of D-shaped core wire (3).

3. The male connector according to claim 2, wherein a continuous insulating material (6) is disposed between the conductive members (4) and the core wire (3), with a minimum of insulating material (6) being provided between the curved part of the D-shaped core wire (3) and the inner surface of the conductive members (4).

4. The male connector (1) according to claim 2, wherein the core wire (3) is made of titanium, the surface of which is oxidized to titanium dioxide.

5. The male connector (1) according to claim 1, wherein said cavity is provided by a longitudinal recess in the mantle surface of the core wire (3).

6. The male connector (1) according to claim 5, wherein a continuous insulating material (6) is disposed between the conductive members (4) and the core wire (3), with a minimum of insulating material (6) being provided between the cylindrical part of the core wire (3) and an inner surface of the cylindrical conductive members (4).

7. The male connector (1) according to claim 1, wherein several cavities are provided by longitudinal recesses in the mantle surface of the core wire (3), and wherein each conductor (5) is disposed in a separate recess.

8. The male connector (1) according to claim 1, wherein several cavities are provided by longitudinal recesses in the mantle surface of the core wire (3), and wherein each recess accommodates at least one conductor (5).

9. The male connector (1) according to claim 1, wherein said cavity is provided by a longitudinal hole in the core wire (3).

10. The male connector (1) according to claim 9, wherein a continuous insulating material (6) is disposed between the conductive members (4) and the core wire (3).

11. The male connector (1) according to claim 1, wherein at least one of the conductors (5) is connected to a proximal end of the corresponding conductive member (4).

12. The male connector (1) according to claim 1, wherein at least one of said conductors (5) is drawn in a loop, which extends towards a proximal end of the male connector (1) before going back to a distal end of a respective conductive member (4), where said conductor (5) is connected.

13. The male connector (1) according to claim 1, wherein the core wire (3) is provided with a layer of insulating material (12).

14. The male connector (1) according to claim 13, wherein the insulating material (12) comprises ceramic particles in a polymer matrix.

15. The male connector (1) according to claim 13, wherein the insulating material (12) comprises a metal oxidized to ceramic state.

16. The male connector (1) according to claim 15, wherein the core wire (3) is made of titanium, the surface of which is oxidized to titanium dioxide.

17. The male connector (1) according to claim 15, wherein the core wire (3) is made of a metal having a coating of aluminum, which is oxidized to $Al_2O_3$.

18. The male connector (1) according to claim 1, wherein the core wire (3) is made of an insulating material.

19. The male connector (1) according to claim 1, wherein the conductors (5) are provided with a layer of insulating material (13).

20. The male connector (1) according to claim 1, wherein the core wire (3) in the male connector (1) is separate from the guide wire core in the guide wire (2).

21. The male connector (1) according to claim 1, wherein the core wire (3) in the male connector (1) is an extension of the guide wire core in the guide wire (2).

22. The male connector (1) according to claim 1, wherein at least two points on the mantle surface of the core wire (3)

are in contact with the inner surface of the conductive members (4), said points having such positions that the core wire (3) is a radially self-positioning core wire (3).

23. The male connector (1) according to claim 1, wherein the core wire (3) has a larger outer circumference when taken normal to a longitudinal direction of extension of the core wire (3) than an outer circumference of the guide wire core section when taken normal to a longitudinal direction of extension of the guide wire core.

24. A male connector (1) for a guide wire (2), wherein
the guide wire (2) comprises a guide wire core including a section that substantially extends through the guide wire (2) substantially from a distal end of the guide wire (2) and substantially to a proximal end of the guide wire (2), wherein
the male connector (1) comprises a core wire (3), a plurality of conductive members (4) spaced apart longitudinally along said core wire (3), and a plurality of conductors (5) disposed along the core wire (3), each of the conductors (5) being connected to a respective conductive member (4), wherein the core wire (3) has such a shape that at least one longitudinal cavity is provided inside the male connector (1), the longitudinal cavity being adapted to remain substantially intact when the male connector (1) is bent, thereby protecting the conductors (5), which are disposed in said cavity, from being damaged if the male connector (1) is bent, wherein the core wire is asymmetrical, and wherein the core wire (3) is stiffer than the section of the guide wire core that substantially extends through the guide wire (2) substantially from the distal end of the guide wire (2) substantially to the proximal end of the guide wire (2).

25. The male connector (1) according to claim 24, wherein the core wire (3) has a larger outer circumference when taken normal to a longitudinal direction of extension of the core wire (3) than an outer circumference of the guide wire core section when taken normal to a longitudinal direction of extension of the guide wire core.

26. A male connector (1) for a guide wire (2), wherein
the guide wire (2) comprises a guide wire core including a section that substantially extends through the guide wire (2) substantially from a distal end of the guide wire (2) and substantially to a proximal end of the guide wire (2), wherein
the male connector (1) comprises a core wire (3), a plurality of conductive members (4) spaced apart longitudinally along said core wire (3), and a plurality of conductors (5) disposed along the core wire (3), each of the conductors (5) being connected to a respective conductive member (4), wherein the core wire (3) has such a shape that at least one longitudinal cavity is provided inside the male connector (1), the longitudinal cavity being adapted to remain substantially intact when the male connector (1) is bent, thereby protecting the conductors (5), which are disposed in said cavity, from being damaged if the male connector (1) is bent, wherein said cavity is located within an extrapolated circumference of the core wire, and wherein the core wire (3) is stiffer than the section of the guide wire core that substantially extends through the guide wire (2) substantially from the distal end of the guide wire (2) substantially to the proximal end of the guide wire (2).

27. The male connector (1) according to claim 26, wherein said cavity is located inside a hollow portion of the core wire (3).

28. The male connector (1) according to claim 27, wherein each the conductors (5) is located inside the hollow portion of the core wire (3).

29. The male connector (1) according to claim 26, wherein the core wire (3) has a larger outer circumference when taken normal to a longitudinal direction of extension of the core wire (3) than an outer circumference of the guide wire core section when taken normal to a longitudinal direction of extension of the guide wire core.

30. A male connector (1) for a guide wire (2), wherein
the guide wire (2) comprises a guide wire core including a section that substantially extends through the guide wire (2) substantially from a distal end of the guide wire (2) and substantially to a proximal end of the guide wire (2), wherein
the male connector (1) comprises a core wire (3), a plurality of conductive members (4) spaced apart longitudinally along said core wire (3), and a plurality of conductors (5) disposed along the core wire (3), each of the conductors (5) being connected to a respective conductive member (4), wherein the core wire (3) has such a shape that at least one longitudinal cavity is provided inside the male connector (1), the longitudinal cavity being adapted to remain substantially intact when the male connector (1) is bent, thereby protecting the conductors (5), which are disposed in said cavity, from being damaged if the male connector (1) is bent, wherein at least one diameter of the core wire when taken on a plane normal to its longitudinal axis is shorter in length than another diameter of the core wire taken on the same plane, and wherein the cavity is adjacent to a surface of the core wire forming a terminus of the shorter diameter, and wherein the core wire (3) is stiffer than the section of the guide wire core that substantially extends through the guide wire (2) substantially from the distal end of the guide wire (2) substantially to the proximal end of the guide wire (2).

31. The male connector (1) according to claim 30, wherein the core wire (3) has a larger outer circumference when taken normal to a longitudinal direction of extension of the core wire (3) than an outer circumference of the guide wire core section when taken normal to a longitudinal direction of extension of the guide wire core.

32. A male connector (1) for a guide wire (2), wherein
the guide wire (2) comprises a guide wire core including a section that substantially extends through the guide wire (2) substantially from a distal end of the guide wire (2) and substantially to a proximal end of the guide wire (2), wherein
the male connector (1) comprises a core wire (3), a plurality of conductive members (4) spaced apart longitudinally along said core wire (3), and a plurality of conductors (5) disposed along the core wire (3), each of the conductors (5) being connected to a respective conductive member (4), wherein the core wire (3) has such a shape that at least one longitudinal cavity is provided inside the male connector (1), the longitudinal cavity being adapted to remain substantially intact when the male connector (1) is bent, thereby protecting the conductors (5), which are disposed in said cavity, from being damaged if the male connector (1) is bent, wherein at least one diameter of the core wire when taken on a plane normal to its longitudinal axis is shorter in length than another diameter of the core wire taken on the same plane, thus representing a shorter diameter, and wherein each of the conductors (5) is disposed adjacent to the surface of the core wire forming a terminus of the shorter diameter, and wherein each of the conductors are located within a distance from the surface of the core wire forming the terminus that is less than the difference in length between the longest diameter and the shorter diameter, and wherein the core wire (3) is stiffer than the section of the guide wire core that substantially extends through the guide wire (2) substantially from the distal end of the guide wire (2) substantially to the proximal end of the guide wire (2).

33. The male connector (1) according to claim 32, wherein the core wire (3) has a larger outer circumference when taken normal to a longitudinal direction of extension of the core wire (3) than an outer circumference of the guide wire core section when taken normal to a longitudinal direction of extension of the guide wire core.

* * * * *